United States Patent [19]

Beran

[11] 4,336,798
[45] Jun. 29, 1982

[54] MEDICAL CORRUGATED RESPIRATORY TUBE

[75] Inventor: Anthony V. Beran, 3802 Teakwood, Santa Ana, Calif. 92704

[73] Assignee: Anthony V. Beran, Costa Mesa, Calif.

[21] Appl. No.: 194,582

[22] Filed: Oct. 6, 1980

[51] Int. Cl.³ .......................................... A61M 16/00
[52] U.S. Cl. ........................ 128/200.14; 128/200.18; 128/204.18; 128/205.23; 128/911; 138/111; 138/122; 138/150; 156/144
[58] Field of Search ...................... 128/200.14, 200.18, 128/200.21, 204.15, 204.17, 200.24, 204.18, 912, 911, 204.13, 205.23; 138/111, 174, 122, 129, 154, 150, 115, 116, 178; 174/15 C; 156/144, 185

[56] References Cited

U.S. PATENT DOCUMENTS 3,117,596 1/1964 Kahn ................................. 138/111
3,856,051 12/1974 Bain ................................. 128/204.28
3,865,106 2/1975 Paluch ................................. 128/911

FOREIGN PATENT DOCUMENTS 684276 4/1964 Canada ................................. 138/111
1171861 1/1959 France ................................. 128/912
2013463 4/1970 France ................................. 128/204.18
335147 9/1930 United Kingdom ................ 138/111

Primary Examiner—Henry J. Recla

[57] ABSTRACT

A plastic medical respiratory conduit is provided having a first tubular helical coil conduit communicating with a first source of fluid. The coil conduit is wrapped with a pliable tape to form a second conduit communicating with a second source of fluid. Resilient couplers can be attached to each end of the conduit to form part of a medical ventilator or humidification system, the resulting ventilator or humidification system providing heretofore unavailable advantages.

13 Claims, 6 Drawing Figures

U.S. Patent    Jun. 29, 1982    4,336,798
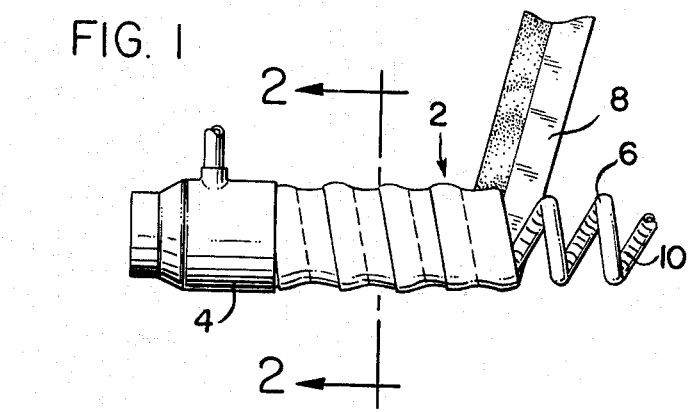
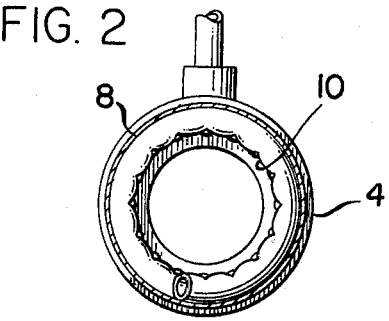
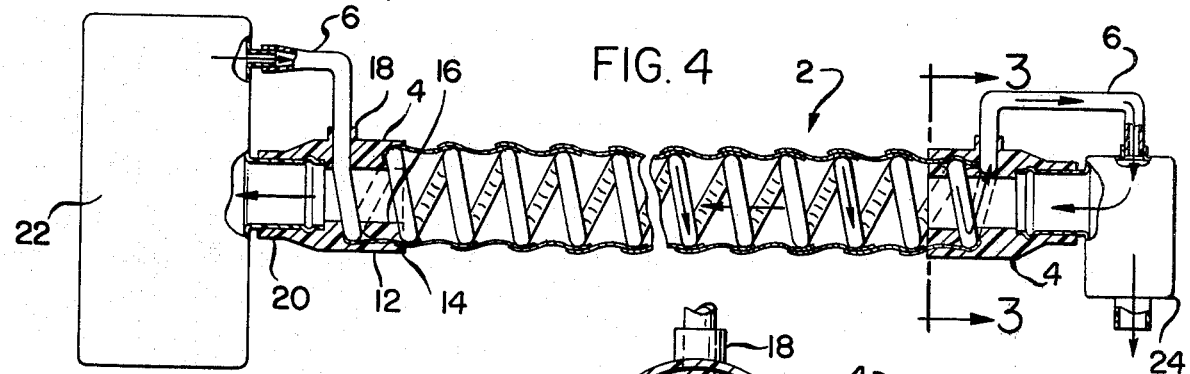
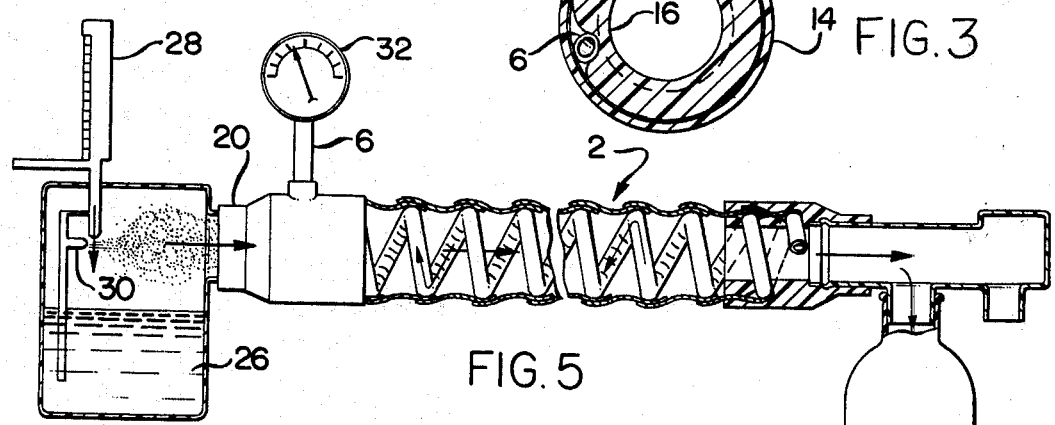
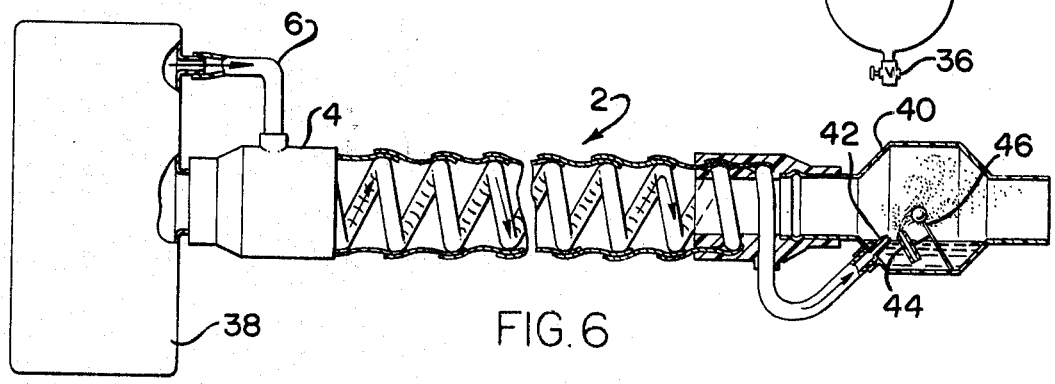

MEDICAL CORRUGATED RESPIRATORY TUBE

BACKGROUND OF THE INVENTION

1. Field of the Invention

The present invention is directed to a medical respiratory tube or conduit for transmitting one or more fluids in an economical manner from or to a patient. More particularly, the present invention is directed to a first coiled conduit forming the peripheral dimensions of a second flexible conduit wherein the second conduit can transmit primary fluid to or from a patient while the first conduit can supplement the transmission of fluid, such as delivering anesthesia gases, or can monitor the pressure of the second conduit. Additionally, the first conduit can transmit inspiratory gases to the patient while the second larger conduit can transmit expiratory gases from the patient.

2. Description of Prior Art

A common requirement in the health industry is control of the inspiratory and expatory respiration of a patient. Frequently, patients are fluidly connected to humidifiers, respirators, incubators, and other forms of respiratory support systems.

An example of a dual conduit system for delivering gas to be breathed by a patient is disclosed in U.S. Pat. No. 3,871,373. In this system, a water-filled tube is looped through the gas conduit with sufficient pressure to cause water vapor to seep through the tube to humidify the gas transmitted to the patient. Of general interest in U.S. Pat. No. 3,902,486, U.S. Pat. No. 4,013,122, and the humidifying incubators disclosed in U.S. Pat. No. 3,070,086 and U.S. Pat. No. 3,529,590.

The high cost of hospital equipment requires respiratory conduits and particularly those which are designed to be disposable to be manufactured in a relatively inexpensive manner. Since these respiratory conduits, however, are part of a life support system for a patient, it is necessary that they have a high degree of reliability. Accordingly, the prior art is still seeking to meet these conflicting demands of the medical industry in providing a respiratory conduit.

SUMMARY OF THE INVENTION

The present invention provides a respiratory corrugated conduit that is not only transparent, flexible and noncollapsible, but is capable of sustaining the respirator pressure in a relatively inexpensive manner while providing an increased thermal insulating property. The conduit is capable of transmitting fluids to and from a patient from a plurality of sources and, further, is capable of monitoring the pressure of fluids communicating with the patient. The respiratory conduit includes a first hollow helical coil that is covered with a pliable tape member to interconnect the helical coils and to form a larger second conduit. A resilient coupler having an annular recess to encompass the end of the conduit can be provided. The resilient coupler can further have a passageway to permit the first helical coil conduit to extend beyond the confines of the primary second conduit.

This respiratory conduit can be combined with a medical ventilator assembly with the larger conduit transmitting pressurized gas and the smaller helical coil conduit communicating with a reservoir of liquid to humidify the gas carried by the second conduit. Alternatively, the conduit can be used in a ventilator system wherein the first hollow helical coil can either supplement the gas delivered to the patient with a second gas such as a source of anesthesia gas, or the hollow helical coil can communicate with the interior of the primary conduit and also with a pressure gauge to indicate the pressure of the transmitted gas at a point adjacent the patient. The first conduit could also be used for the inspiratory conduit of a respirator system, while the second conduit could form the expiratory conduit.

The objects and features of the present invention are set forth in the appended claims. The present invention may be best understood by reference to the following description, taken in conjunction with the accompanying drawings in which like numerals indicate the like parts.

BRIEF DESCRIPTION OF THE DRAWINGS

FIG. 1 is a side view of one end of a corrugated respiratory tube and coupler with the tube partially disassembled;

FIG. 2 is a cross sectional view taken along the lines 2—2 of FIG. 1;

FIG. 3 is a cross sectional view of one end of a coupler taken along the lines 3—3 of FIG. 4.

FIG. 4 is a partial cross sectional view of a respiratory tube used in an anesthesia delivery system;

FIG. 5 is a partial cross sectional view of the corrugated respiratory tube used in a continuous positive airway pressure and humidification system; and FIG. 6 is a partial cross sectional view of the corrugated respiratory tube used in a ventilator and humidification system.

DESCRIPTION OF THE PREFERRED EMBODIMENTS

The following specification, taken in conjunction with the drawings, sets forth the preferred embodiment of the present invention in such a manner that any person skilled in the medical equipment field can use the invention. The embodiments of the invention disclosed herein are the best modes contemplated by the inventor for carrying out his invention in a commercial environment, although it should be understood that various modifications can be accomplished within the parameters of the present invention.

Corrugated medical tubing is used to connect humidifiers, respirators, and other respiratory support systems to patients. Some of the basic requirements for corrugated medical tubing are that it be transparent, flexible, noncollapsible, and finally, capable of maintaining the tube wall compliance to sustain the respirator pressure. The high cost of medical labor in hospitals plus the desire to prevent any contamination between respective patients imposes an additional requirement that the medical corrugated tubing be inexpensive enough to be disposed of without requiring sterilization for secondary use. However, since the medical corrugated tubing is part of a life support system, it must be highly reliable and of a relatively sturdy construction.

The present invention has not only met the above criteria, but has provided an improved medical corrugated tubing with added capacities.

Referring to FIG. 1, the improved medical corrugated respiratory tube 2 of the present invention is disclosed connected to a resilient coupler 4. The dimensions and configuration of the coupler are such to be complimentary for appropriate connections with auxiliary respiratory equipment, such as ventilators and anesthesia delivery and retrieving apparatus.

The corrugated tubing 2 comprises an inner helical coil of a medical grade polyethylene plastic tubing 6, for example, having a 0.125 inch inner diameter and 0.1875 inch outer diameter. The coil 6 is appropriately wrapped around a mandrel (not shown) to form approximately two to three loops of the coil per inch and is then wrapped by a polyvinyl chloride medical grade plastic tape of approximately 0.008 inches in thickness and 0.625 inches in width. A medically acceptable glue such as methyl ethyl ketone, or any other medically acceptable polyvinyl chloride solvent is initially applied to at least one edge of the tape 8 as shown in FIG. 1, to bind it together in a helical configuration to form the outer membrane surface of the respiratory tube 2.

Thus, the present invention provides a first hollow helical coil 6 that is capable of transmitting fluid along its length which is covered by a pliable tape covering member 8 that interconnects the helical coils 6 to form a larger primary interior conduit. The spacing of the loops of coil 6 and the resulting resiliency characteristics of the coil conduit as restrained by the tape 8 define sufficient parameters to provide an approximately constant cross sectional wall flow path for a primary conduit in a respiratory or ventilating system. When winding the helical coil configuration about a mandrel, the relative dimensions chosen are such to provide a plurality of regularly spaced creases 10 extending substantially parallel to the longitudinal axis of the primary conduit. The outer circumference of the coil 6 remains substantially smooth and is complimentary to supporting the flexible and pliable outer tape 8. The provision of the regularly spaced parallel creases 10 contribute to the flexibility of the respiratory tube 2 while minimizing any potential for a crimp or predisposition of a crimp at any specific point along the medical tube 2.

Referring to FIGS. 2 and 4, the resilient coupler 4 is disclosed. This coupler 4 can be injection molded. One end of the coupler 4 is particularly adapted for receiving the helical coil 6 while the other end has been designed for interfacing with a coupler of a respirator or humidifier. The helical coil end of the coupler 12 is cross sectionally bifurcated to provide a pair of concentric overlapping tubular extensions 14 and 16. The respective interior surfaces of these tubular extensions 14 and 16 that face each other define a helical tubular passageway that is adapted to receive and encompass an extension of the coil 6 beyond the confines of the flow path parameter of the primary conduit formed by the tape 8. Additionally, the inner tubular extension 14 defines a bore which permits an extension of the coil 6 to extend through an exterior of the coupler 4. This bore terminates in an exterior raised flange 18. Alternatively, the coil 6 could terminate within the bore (not shown) and thereby provide a universal coupling that could be supplemented with a secondary tube (not shown) designed for any specific application and connection, e.g., pressure gauge, respirator, etc.

The resilient coupler 4 further includes a second coupler end 20 having an interior conduit surface that is complimentary to and capable of providing an annular recess to provide an interlocking fit with any sealing bead on a tubular fitting of a respirator apparatus. Additional configurations are possible to compliment a specific fitting.

The advantages of forming the medical respiratory tubing 2 with a hollow coil 6 extend beyond simply providing a highly reliable noncollapsible fluid conduit for a primary delivery of fluid. The coil 6 has the capacities of providing a secondary conduit for either direct transmission of fluid to a patient or for providing certain monitoring or auxiliary functions with regard to the delivery of the primary fluid to the patient. For example, coil 6 could deliver oxygen to the patient as an inspiratory gas while the larger primary conduit could provide a passageway for expiratory gases at a lower pressure resistance.

Referring to FIG. 4, the corrugated respiratory tube 2 of the present invention is disclosed connected to an anesthesia delivery and retrieving system 22. The secondary conduit coil 6 is operable for the delivery of anesthesic gases such as oxygen, nitric oxide, halothanes, etc., while the primary conduit is utilized for both inspiration and expiration from the patient. An auxiliary coupler 24 can in turn be connected to an endotracheal tube (not shown) that is connected to a patient to permit his upper air passages to be bypassed.

FIG. 5 discloses a partial cross sectional view of another medical ventilator system for providing positive pressure breathing to a patient with the tube 2 of the present invention. In this regard, a humidifier 26 is connected directly to the coupler end 20. A flow meter 28 measures the flow of air from a gas source into the humidifier. The humidifier nozzle 30 draws the liquid upward as a result of the ventori pressure created and disburses fluid particles into the air stream. The exterior end of the coil 6, adjacent the humidifier, extends above and beyond the coupler 4 and is connected to a pressure gauge 32 for constant measuring of the proximal airway pressure at the end of the tubing 2. A compliance bag 34 and bleed valve 36 can be conveniently attached adjacent the second coupler, and the interior end of coil 6 is open to the primary conduit adjacent the compliance bag 34.

Referring to FIG. 6, a medical ventilator and humidification system is disclosed. The ventilator 38 such as a Bird ventilator manufactured by the Bird Ventilator Company of Palm Springs, Calif., is connected to the medical tubing 2 of the present invention through the resilient coupler 4. The secondary conduit coil 6 is connected to a source of positive pressure air from the ventilator 38 at one end, and is further connected to a humidifier assembly 40 at the other end. The disclosure in FIG. 6 only shows the inspiratory connection to the patient and not the expiratory connection. A nozzle 42 directs a flow of air, for example, having a pressure of 45 psi across a fluidic conduit 44 to cause the liquid, which can include medication, to be drawn upward and entrapped in the air stream in the form of particles. A barrier breaker or dispenser 46 is designed to ensure a thorough mixing of the fluidic medication into the air stream of the inspiration flow that is conducted by the medical tube from the ventilator 38.

A subtle advantage of the present invention resides in the increased thermal insulating properties resulting from the peripheral arrangement of the helical coil 6. The helical coil 6 acts as an insulator for a significant portion of the interior area of the tube 2, and thereby reduces the outward transmission of heat over a conventional respiratory conduit. As a result, the control of heat content of inspiratory gas to proximate the body temperature is easier to achieve with a corresponding reduction in condensation formed within the tube 2.

Obviously, many different modifications and variations of the present invention are possible in light of the above description. It is, therefore, to be understood that the scope of the present invention should be determined solely from the following claims:

What is claimed is:

1. A medical respiratory conduit for transmission of fluids to or from a patient comprising:
   a first hollow medical grade plastic helical coil conduit having an inlet and an outlet for communicating with a fluid flow, the outlet always remaining open to accommodate fluid movement, and
   a substantially transparent flexible medical grade plastic tape member interconnecting the helical coils to form a larger second conduit having an inlet for communicating with a source of fluid and an outlet for enabling the exit of the fluid, the spacing of the coils and resiliency characteristics of the coil conduit defining sufficient parameters to support an approximately constant cross sectional wall flow path along the second conduit while providing thermal insulation space between the interior of the second conduit and the ambient surroundings, the outer circumference of the helical coils is substantially smooth and the plastic helical tape member overlaps and adheres to itself adjacent the smooth outer circumference to form a fluid tight second conduit.

2. The invention of claim 1 further including a resilient coupler having a first portion with an annular recess that encompasses one end of the second conduit and a passageway for extending the first helical conduit beyond the confines of the constant cross-sectional wall flow path.

3. The invention of claim 2 wherein the resilient coupler includes a second portion having an annular recess to provide an interlocking fit with a sealing bead on a tubular fitting.

4. The invention of claim 2 wherein the resilient coupler includes an annular recess having a helical cavity complimentary to the helical coil pitch.

5. The invention of claim 1 wherein the helical coil conduit is an elongated plastic tube.

6. A plastic medical respiratory conduit for controlling the transmission of fluids to or from a patient comprising:
   a first tubular medical grade plastic helical coil conduit having an inlet capable of communication with a source of fluid and an outlet, the inner circumference of the helical coil including a plurality of regularly spaced creases extending substantially parallel to the helix formed by the first helical coil conduit while the outer circumference of the helical coil is substantially smooth;
   a pliable medical grade plastic helical tape member overlapping and adhering to itself adjacent to the smooth outer circumference of the helical coil to form a second conduit having an inlet for communication with a source of fluid and an outlet for enabling the exit of the fluid, the first tubular helical coil defining the structural configuration of the second conduit and the plastic tape member completing the perimeter of the flow path of the second conduit, and
   a first coupler attached to one of the second conduit adjacent said helical coil inlet, a second coupler attached to the other end of said conduit adjacent said helical coil outlet, each said couplers having a helical recessed annular cavity complimentary to the helical coil pitch in which the helical coil is received and a passageway therethrough for providing fluid communication through the confines of the flow path perimeter of the second conduit, and the inlet and outlet end portions of said helical coil conduit extend through a sidewall of said first and second couplers, respectively.

7. The invention of claim 6 wherein the pitch of the helical coil is approximately 2 to 3 coils per inch.

8. A medical ventilator and humidification system comprising:
   a ventilator assembly for generating pressurized gas;
   a first hollow helical coil conduit having an inlet communicating with a first source of pressurized gas fluid from the ventilator assembly and an outlet, the inner circumference of the helical coil includes a plurality of regularly spaced creases extending substantially parallel to a longitudinal axis of the helix formed by the first helical coil conduit while the outer circumference of the helical coils are substantially smooth;
   a pliable covering member of substantially transparent flexible plastic tape interconnecting the helical coils in an overlapping manner to form a larger second conduit having an inlet communicating with a second source of pressurized gas from the ventilator assembly and an outlet for enabling the exit of the gas from the ventilator assembly, the spacing of the coils and resiliency characteristics of the coil conduit defining sufficient parameters to provide a flow path along the second conduit;
   a reservoir of fluid having a gas flow path therethrough connected to the outlet of the second conduit;
   a nozzle member connected to the reservoir and to the outlet of the helical coil conduit and communicating with the flow path of the reservoir to vaporize the fluid therein for introduction into the gas carried by the second conduit.

9. A medical ventilator system comprising:
   a ventiltor assembly for generating pressurized gas, and removing exhausting gas;
   a first hollow helical coil conduit having an inlet connected to receive pressurized gas from the ventilator assembly and an outlet; the inner circumference of the helical coil includes a plurality of regularly spaced creases extending substantially parallel to a longitudinal axis of the helix formed by the first helical coil conduit while the outer circumference of the helical coils are substantially smooth;
   a pliable covering member of substantially transparent flexible plastic tape interconnecting the helical coils to form a second conduit having an inlet communicating with the ventilator assembly for expanding gas therefrom and an outlet, and
   means connected to the outlet of said second conduit for fluidic connection to the respiratory tract of a patient, the outlet of said first hollow helical coil being connected to the means for fluidic connection to deliver a respiratory flow of pressurized gas to a patient, the second conduit being connected between the ventilator assembly and the means for fluidic connection for removing exhausting gas from a patient.

10. The invention of claim 9 further including a resilient coupler having a first portion with an annular recess that encompasses one end of the second conduit and a passageway for extending the first helical coil conduit beyond the confines of the second conduit for connection with the means for fluidic confines of the second conduit for connection with the means for fluidic connection.

11. The invention of claim 9 wherein the ventilator assembly is connected to a source of anesthesia gas and the first hollow helical coil delivers it to the interior of the second conduit.

12. A medical ventilator system for providing positive gas pressure comprising:

a ventilator assembly for generating pressurized gas;

a first hollow helical coil conduit having an inlet and an outlet, the inner circumference of the helical coil includes a plurality of regularly spaced creases extending substantially parallel to a longitudinal axis of the helix formed by the first helical coil conduit while the outer circumference of the helical coils are substantially smooth;

a pliable covering member of substantially transparent flexible plastic tape interconnecting the helical coils to form a larger second conduit having an inlet communicating with a source of pressurized gas from said ventilator assembly and an outlet for enabling the exit of the gas, the spacing of the coils and resiliency characteristics of the coil conduit defining sufficient parameters to provide a wall flow path along the second conduit, means connected to the outlet of said second conduit for fluidic connection to the respiratory track of a patient; and means for measuring pressure, the hollow helical coil inlet connected to the means for measuring pressure and the helical coil outlet communicating with the flow path of the second conduit.

13. A plastic medical respiratory conduit for controlling the transmission of fluids to or from a patient comprising:

a first tubular medical grade plastic helical coil conduit having an inlet and an outlet capable of communication with a fluid flow, the inner circumference of the helical coil including a plurality of regularly spaced creases extending substantially parallel to the helix formed by the first helical coil conduit while the outer circumference of the helical coil is substantially smooth;

a pliable medical grade plastic helical tape member overlapping and adhering to itself adjacent to the smooth outer circumference of the helical coil to form a second conduit having an inlet for communication with a source of fluid and an outlet for enabling the exit of the fluid, the first tubular helical coil defining the structural configuration of the second conduit and the plastic tape member completing the perimeter of the flow path of the second conduit, and a first coupler attached to one end of the second conduit adjacent said helical coil inlet, a second coupler attached to the other end of said second conduit adjacent said helical coil outlet, each said couplers having a helical recessed annular cavity complimentary to the helical coil pitch in which the helical coil is received and a passageway therethrough for providing fluid communication through the confines of the flow path perimeter of the second conduit, and the inlet end portion of said helical coil conduit extends through a sidewall of said first coupler and the outlet end portion of the helical coil conduit terminates within the passageway of said second coupler.

* * * * *